United States Patent [19]

Rekers

[11] Patent Number: 5,049,605

[45] Date of Patent: Sep. 17, 1991

[54] BIS(3,4-DIALKYLBENZYLIDENE) SORBITOL ACETALS AND COMPOSITIONS CONTAINING SAME

[75] Inventor: John W. Rekers, Spartanburg, S.C.

[73] Assignee: Milliken Research Corporation, Spartanburg, S.C.

[21] Appl. No.: 409,912

[22] Filed: Sep. 20, 1989

[51] Int. Cl.[5] .................. C07D 323/04; C07D 493/00; C08K 5/05
[52] U.S. Cl. ..................................... 524/108; 549/364
[58] Field of Search ......................... 524/108; 549/364

[56] References Cited

U.S. PATENT DOCUMENTS

| | | | |
|---|---|---|---|
| 3,721,682 | 3/1973 | Murai et al. | 549/43.3 |
| 4,314,039 | 2/1982 | Kawai et al. | 525/1 |
| 4,371,645 | 2/1983 | Mahaffey, Jr. | 524/108 |
| 4,845,137 | 7/1989 | Williams et al. | 524/108 |

FOREIGN PATENT DOCUMENTS

| | | | |
|---|---|---|---|
| 0045934 | 4/1981 | Japan | 524/108 |
| 0129036 | 8/1983 | Japan | 524/108 |
| 0157840 | 9/1983 | Japan | 524/108 |
| 0164348 | 9/1984 | Japan | 524/108 |
| 0090238 | 5/1985 | Japan | 524/108 |
| 1019646 | 1/1986 | Japan | 524/108 |
| 62-4289 | 1/1987 | Japan | . |
| 2115049 | 5/1987 | Japan | 524/108 |
| 3075048 | 4/1988 | Japan | 524/108 |

Primary Examiner—Kriellion S. Morgan
Attorney, Agent, or Firm—Timothy J. Monahan; H. William Petry

[57] ABSTRACT

Bis(3,4-dialkylbenzylidene) sorbitol acetals are provided for the formula:

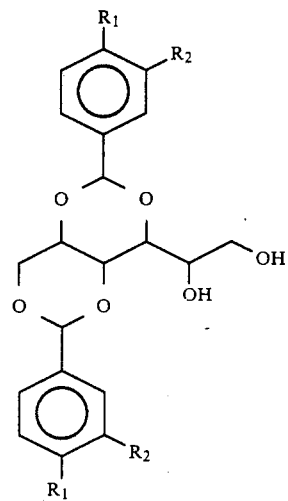

in which $R_1$ and $R_2$ are independently selected from lower alkyl groups containing 1-4 carbon atoms, or together form a carbocyclic ring containing up to 5 carbon atoms.

4 Claims, No Drawings

BIS(3,4-DIALKYLBENZYLIDENE) SORBITOL ACETALS AND COMPOSITIONS CONTAINING SAME

This invention relates to plastic additives which are useful as nucleating agents and which are especially useful for improving the optical properties of polymeric materials. More particularly, this invention relates to certain bis-dialkylbenzylidene sorbitol acetals and polymer compositions thereof which are useful as materials for food or cosmetic containers and packaging because they do not impart an objectionable taste or odor to the packaged material.

It is known that the addition of nucleating agents to certain polymeric materials, such as polyolefins, can provide both improved optical and physical properties to the resin. Furthermore, it is known that organic nucleating agents, such as dibenzylidene sorbitol as disclosed in U.S. Pat. No. 4,016,118 to Hamada, et al. are more effective than much higher melting nucleating agents, such as sodium benzoate, in improving the clarity of products fabricated from polyolefins, such as sheet, film, bottles, or injection molded parts. Generally, organic nucleators are more easily dispersed during processing and thus provide a more uniform effect.

The dibenzylidene sorbitol (DBS) nucleating agent mentioned above provides a highly beneficial combination of cost and performance. It provides excellent clarity enhancement in polypropylene copolymer and is suitable for food contact packaging because it does not affect the taste of packaged foods. However, DBS has certain practical deficiencies such as a tendency to plate-out at high processing temperatures and insufficient clarity improvement in certain applications, such as in thick parts fabricated from polypropylene homopolymer.

In order to overcome these deficiencies, many derivatives of DBS in which the aromatic rings are substituted with various groups have been proposed. Generally, substituted derivatives of DBS may overcome the processing and performance disadvantage mentioned above. In particular, alkyl and halogen substituted derivatives have been especially advantageous in this regard.

Thus, Mahaffey, in U.S. Pat. No. 4,371,645, discloses compounds of the general formula:

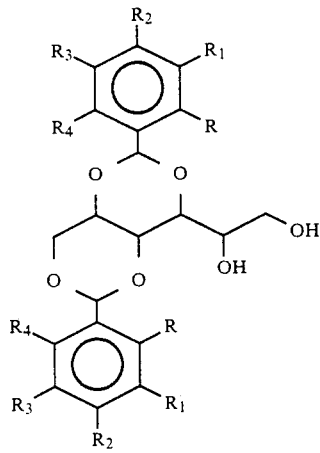

(I)

in which R, $R_1$, $R_2$, $R_3$, and $R_4$ are selected from H, lower alkyl, hydroxy, methoxy, mono- and di- alkylamino, nitro, and halogen, provided that at least one is halogen. Although these compounds may provide excellent clarity and processing characteristics in polyolefin compositions, the required presence of halogen may be undesirable, particularly in food contact applications.

Kawai, et al. in U.S. Pat. No. 4,314,039, discloses monosubstituted DBS derivatives having the formula:

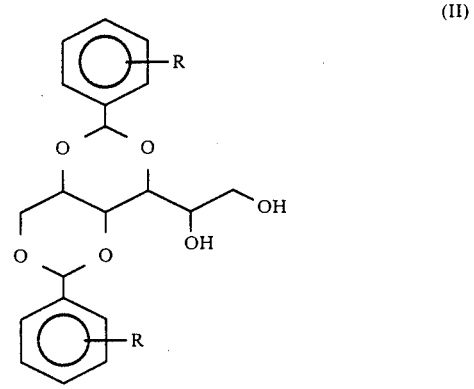

(II)

in which R represents an alkyl group having 2 to 18 carbon atoms. In addition, Murai, et al. in Japanese Patent Application No. 54[1979]-121696 discloses compounds with improved nucleation properties having the general formula:

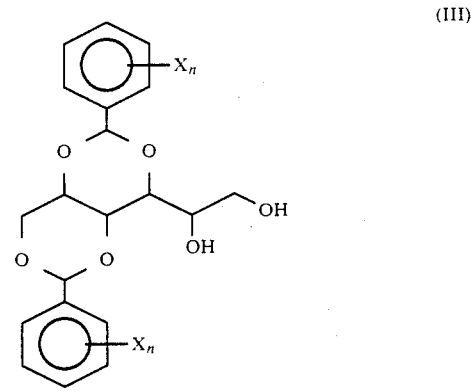

(III)

in which X is selected from alkyl groups of 1–3 carbon atom or halogen, and n is an integer from 1–3, but when X is methyl, n is 2 or 3.

Although certain of these derivatives prepared from mono or di-substituted benzaldehydes may provide improved nucleation and clarification properties, in addition to easier processing in polyolefins, these compounds are generally not suitable for food contact applications and food packaging due to the transfer of unacceptable taste and odor to the contained material. In fact, in order to overcome this problem, Oteki, et al. in Japanese Application No. 62[1987]-4289 proposes the use of organo amine co-additives to alleviate the taste and odor problem. Unfortunately, this approach is complicated by the taste and odor of the amine co-additives themselves. It would be far preferable to have nucleators which inherently do not possess these deficiencies.

In regard to the previously disclosed derivatives prepared from dialkyl substituted benzaldehydes, it is to be noted that no disclosures have been made which suggest that the positional substitution of the alkyl groups may be related to the performance of the additive in applications where taste or odor transfer to packaged materials is a consideration. In fact, previous disclosures do not disclose substitution patterns at all, indicating that this variable was not recognized as important to the performance of the clarifying agents. We have found, quite surprisingly, that the positional substitution on the aromatic rings of bis-dialkylbenzylidene sorbitols is critical to the performance of these clarifying agents, especially with regard to taste and odor transfer in food contact applications.

It is the object of this invention to provide effective bis-dialkylbenzylidene sorbitol nucleating agent compositions which inherently overcome the taste and odor deficiencies of prior art compounds. Accordingly, polyolefin plastic compositions are provided which possess excellent clarity and very low taste and odor transfer properties.

The position of alkyl group substitution on bis-dialkylbenzylidene sorbitols is critical to the invention. Thus, acetals which contain lower alkyl groups in the 3 and 4 positions on the benzylidene ring provide substantially improved taste and odor transfer properties relative to both the mono-4-alkyl substituted derivatives of Kawai and the di-alkyl derivatives of Mursi with different substitution patterns on the aromatic rings. In addition, we have found that if the alkyl groups in the 3 and 4 position together form a carbocyclic ring, particularly advantageous taste and odor transfer properties result.

The nucleating agents of the present invention can be represented by the following structural formula, for which no stereochemistry is implied:

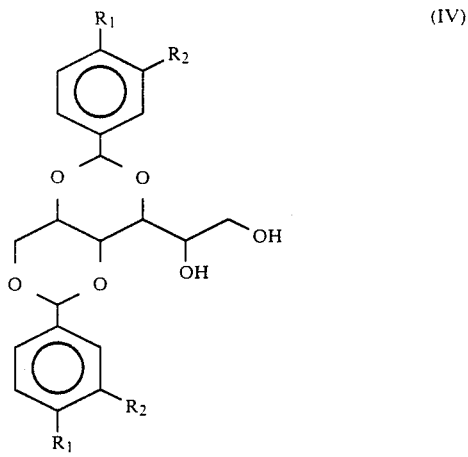

in which $R_1$ and $R_2$ are independently selected from lower alkyl groups containing 1-4 carbon atoms, or together form a carbocyclic ring containing up to 5 carbon atoms.

As mentioned previously, the 3,4-dialkyl substitution pattern is of paramount importance for obtaining compositions with taste and odor transfer properties suitable for food packaging and food container applications. Isomeric di-alkyl derivatives with substitution other than 3,4 and mono substituted derivatives with the same or higher molecular weight have much poorer taste and odor transfer characteristic in polyolefin compositions. This is demonstrated in the Examples.

The substituted bis-dialkylbenzylidene sorbitol acetals of the present invention are a condensation product of sorbitol and a dialkyl substituted benzaldehyde. The benzaldehyde is substituted in both the 3 and 4 positions (meta and para) with alkyl groups containing 1 to 4 carbon atoms. It may be preferable that the alkyl groups at the 3 and 4 position together form a carbocyclic ring containing up to five carbon atoms. Examples of suitable substituted benzaldehydes include 3,4-dimethylbenzaldehyde, 4-ethyl-3-methylbenzaldehyde, 3,4-diethylbenzaldehyde, 3-butyl-4-methylbenzaldehyde, 3,4-di-isopropylbenzaldehyde, and 3,4-di-n-propylbenzaldehyde, of which 3,4-dimethylbenzaldehyde is most preferable. Examples of suitable aldehydes in which the alkyl group at the 3 and 4 positions together form a ring include Indan-5-carboaldehyde, 5,6,7,8-tetrahydro-2-naphthaldehyde, 5-methyl-5,6,7,8-tetrahydro-2-naphthaldehyde, and 5-methyl-5,6,7,8-tetrahydro-2-naphthaldehyde, of which 5,6,7,8-tetrahydro-2-naphthaldehyde (also called 2-tetralin aldehyde) is preferred. Generally, the carbocyclic derivatives are preferred over the non-carbocyclic aldehydes.

The di-acetals of the present invention may be conveniently prepared by a variety of techniques, some of which are known in the art. Generally, such procedures employ the reaction of one mole of D-sorbitol with about two moles of aldehyde in the presence of an acid catalyst. The temperature employed in the reaction will vary widely depending upon the characteristics, such as melting point, of the aldehyde or aldehydes employed as a starting material in the reaction. The reaction medium may be an aqueous medium or a non-aqueous medium. One very advantageous method which can be employed to prepare the di-acetals of the invention is described in U.S. Pat. No. 3,721,682, to Murai, et al. (New Japan Chemical Company Limited), the disclosure of which is hereby incorporated herein by reference. While the disclosure of the patent is limited to benzylidene sorbitols, it has been found that the di-acetals of the present invention may also be conveniently prepared by the method described therein.

The di-acetals of sorbitol of the present invention prepared by the above techniques may contain a minor or even a major portion of by-product mono-acetal and tri-acetal as impurities. Although it may not always be necessary to remove these impurities prior to incorporation of the diacetal into the polyolefin, it may be desirable to do so and such purification may serve to enhance the transparency of the resin produced thereby. Purification of the di-acetal may be accomplished, for instance, by removal of tri-acetal impurities by the extraction thereof with a relatively non-polar solvent. By removal of the impurities, the product may be purified so that the amount of di-acetal in the additive composition contains at least about 90 percent and even up to about 95 percent di-acetal or more.

The proportion of di-acetal in the composition of this invention is an amount sufficient to improve the transparency of the composition, generally from about 0.01 to about 2 percent by weight, preferably about 0.1 to about 1 percent by weight, based upon the total weight of the composition may be provided. When the content of di-acetal is less than about 0.01 percent by weight, the resulting composition may not be sufficiently improved in respect to transparency characteristics. When the content of di-acetal is increased beyond about 2 percent by weight, no additional advantage can be observed.

The bis-dialkylbenzylidene sorbitols of the present invention may be used in polymers for which nucleation may have beneficial effects, especially for such polymers which may be used in food contact applications, or in applications where taste and odor transfer characteristics are a consideration.

The polyolefin polymers of the present invention may include aliphatic polyolefins and copolymers made from at least one aliphatic olefin and one or more ethylenically unsaturated comonomers. Generally, the comonomer, if present, will be provided in a minor amount, e.g., about 10 percent or less or even about 5 percent or less, based upon the weight of the polyolefin. Such comonomers may serve to assist in clarity improvement of the polyolefin, or they may function to improve other properties of the polymer. Examples include acrylic acid and vinyl acetate, etc. Examples of olefin polymers whose transparency can be improved conveniently according to the present invention are polymers and copolymers of aliphatic monoolefins containing 2 to about 6 carbon atoms which have an average molecular weight of from about 10,000 to about 2,000,000, preferably from about 30,000 to about 300,000, such as polyethylene, linear low density polyethylene, polypropylene, crystalline ethylenepropylene copolymer, poly(1-butene), and polymethylpentene. The polyolefins of the present invention may be described as basically linear, regular polymers which may optionally contain side chains such as are found, for instance, in conventional, low density polyethylene.

Other polymers which may benefit from the nucleation and clarification properties of the sorbitol acetals of the present invention include polyethylene terephthalate, glycol modified polyethylene terephthalate, polybutylene terephthalate, and nylons, among others.

The olefin polymer or copolymer used in the composition of the present invention is crystalline, and the diffraction of light caused by micro crystals contained in it is considered to be responsive for the deterioration of the transparency of the polymer. It is thought that the di-acetal functions in the composition to reduce the size of the microcrystals thereby improving the transparency of the polymer.

The composition of the present invention can be obtained by adding a specific amount of the di-acetal directly to the olefin polymer or copolymer, and merely mixing them by any suitable means. Alternatively, a concentrate containing as much as about 20 percent by weight of the di-acetal in a polyolefin masterbatch may be prepared and be subsequently mixed with the resin.

Other additives such as a transparent coloring agent or plasticizers (e.g., dioctyl phthalate, dibutyl phthalate, dioctyl sebacate, or dioctyl adipate), can be added to the composition of the present invention so long as they do not adversely affect the improvement of transparency of the product. It has been found that plasticizers such as those exemplified above may in fact aid in the improvement of the transparency by the di-acetal.

With regard to other additives it may also be desirable to employ the di-acetals disclosed above in combination with other conventional additives having known transparency improving effects such as, for instance, para-t-butylbenzoic acid, its salts, low molecular weight waxy polypropylene and the like. It may even be desirable to provide the particular di-acetals of the present invention in the polyolefin composition in combination with the previously described dibenzylidene sorbitol additive disclosed in U.S. Pat. No. 4,016,118. In such applications, generally at least about 10 percent, preferably about 25 percent, or even about 50 percent or more of the clarity improving component will be the di-acetals of the present invention, with the remained being comprised of other known clarifying agents, plasticizers, etc.

The compositions of the present invention may be obtained by adding the bis-dialkylbenzylidene sorbitol acetal to the polymer or copolymer, and merely mixing the resultant composition by any suitable means. The composition may then be processed and fabricated by extrusion, molding, thermoforming, and the like into a fabricated article.

Other additives may also be used in the composition of the present invention, provided they do not interfere with the primary benefits of the invention. It may even be advantageous to premix these additives or similar structures with the nucleating agent in order to reduce its melting point and thereby enhance dispersion and distribution during melt processing. Such additives are well known to those skilled in the art, and include plasticizers, lubricants, catalyst neutralizers, antioxidants, light stabilizers, colorants, other nucleating agents, and the like. Some of these additives may provide further beneficial property enhancements, including improved aesthetics, easier processing, and improved stability to processing or end use conditions.

The compositions of the present invention are suitable as additives to improve the clarity of packaging materials and container materials for cosmetics, foodstuffs, and the like, because they give film, sheet, and other fabricated articles having excellent transparency and physical properties without imparting a detrimental taste or odor to the contained material.

The following Examples further illustrate the invention but are not to be construed as limiting the invention as defined in the claims appended hereto. Unless otherwise indicated all parts and percentages are by weight.

EXAMPLE 1

The following procedure illustrates the general method for preparing the bis-dialkylbenzylidene sorbitol acetals of the present invention.

A one liter four-necked cylindrical shaped reaction flask equipped with a Dean-Stark trap, condenser, thermometer, nitrogen inlet, and a mechanical stirrer was charged with 37.5 g of sorbitol (0.206 moles) 300 ml of cyclohexane, 54.9 g of 3,4-dimethyl benzaldehyde (0.41 moles), 1 g of p-toluenesulfonic acid, and 200 ml of methanol. The reaction was stirred and heated under reflux with removal of water through the Dean-Stark trap. The reaction becomes very thick and additional solvent is added as needed. After about six hours, the reaction is cooled, neutralized with ammonium hydroxide, and filtered. The wet cake is washed thoroughly with water and isopropyl alcohol, dried in a vacuum oven at 90° C. to give 52.2 g of bis-1,3,2,4-(3',4'-dimethylbenzylidene)sorbitol, m.p. 225°-260°. The purity was about 90% as judged by HPLC, and the $^1$H NMR, $^{13}$C NMR, and IR spectra were consistent with the proposed structure.

EXAMPLES 2-9

A variety of bis-alkylbenzylidene sorbitols were prepared using processes similar to the one described in Example 1 above. The structures of these derivatives are shown in Table 1 below. All products had NMR and IR spectra consistent with the indicated structures, and purities of at least 80% as indicated by HPLC.

TABLE 1

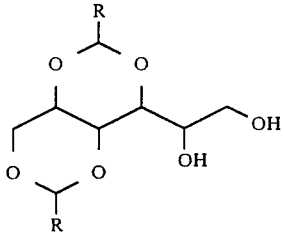

| Example # | R | MW | (°C.) m.p. |
|---|---|---|---|
| 1 | 2,3-diMe-phenyl | 414 | 225–260 |
| 2 | 2,4-diMe-phenyl | 414 | 205–213 |
| 3 | 3,4-diMe-phenyl | 414 | 218–238 |
| 4 | 4-Me-phenyl | 386 | 245–248 |
| 5 | 4-Et-phenyl | 414 | 230–235 |
| 6 | 4-i-Pr-phenyl | 440 | 160 |
| 7 | 4-i-Bu-phenyl | 470 | 160 |
| 8 | tetrahydronaphthyl | 466 | 230–234 |
| 9 | phenyl | 358 | 218–220 |

*No stereochemistry implied

EXAMPLE 10

This Example demonstrates the utility as clarifying agents in polypropylene copolymer of the nucleating additives within the scope of the present invention. The products from Examples 1–9 were compounded into polypropylene random copolymer (ca. 3% ethylene content). The following formulation was used:

| | |
|---|---|
| Clarifying agent (Examples 1–10) | 0.25% |
| Ethyl 330 (a hindered phenol anitoxidant available from Ethyl Corp.) | 0.08% |
| Calcium stearate | 0.08% |
| Polypropylene random copolymer | 99.59% |

The additives and resin were dry blended in a mechanical mixer, extruded through a single screw extruder at 470° F. and pelletized. Step plaques (2×3"; 0.050 and 0.085" thick) were prepared by injection molding at 420°–430° F. The clarity of each sample was obtained by measuring the percent haze through the 0.050" thick section using a Hunter Hazemeter. The clarity obtained from the sorbitol acetal derivatives of Examples 1–10 is shown in Table 2.

TABLE 2

| Clarifying Agent | % Haze* | Comment |
|---|---|---|
| Example 1 | 7–8 | Present invention |
| Example 2 | 13 | Comparative example |
| Example 3 | 21 | Comparative example |
| Example 4 | 8 | Comparative example |
| Example 5 | 10 | Comparative example |
| Example 6 | 45 | Comparative example |
| Example 7 | 44 | Comparative example |
| Example 8 | 7–8 | Present invention |
| Example 9 | 13 | Comparative example |

*average of 10 specimens

EXAMPLE 11

This Example demonstrates the low taste transfer characteristics of the bis(3,4-dialkylbenzylidene) sorbitol acetals within the scope of the present invention.

The resin sample plaques prepared in Example 10 were tested for taste transfer to water. Three plaques from each formulation were immersed in 300 ml of distilled water in one pint jars (8 ml water/in$^2$ plastic surface). The jars were sealed and aged in an oven for five days at 120° F. The plaques were removed and the taste of the water exposed to each sample was evaluated by a taste panel. To establish the validity of the test, water exposed to plaques containing no clarifying agent and water not exposed to plaques were also included as controls.

The taste panel consisted of five persons, and the method of blind pair comparison of the samples was used. Because of the large number of formulations to be evaluated, the test was conducted in three parts of five water samples each. Some of the formulations were tested twice for cross comparison purposes.

The five water samples for each test were portioned into a suitable number of small paper cups, and each panelist compared four pairs without knowing the identity of any of the samples. The panelist determined which sample had the least taste (most like pure water), and the difference between the samples of the pair was rated on a scale of 0 to 10 (0=no difference, 10=very large difference).

The data was then arranged on a matrix of all possible paired comparisons, such that the value of each point in the matrix represented the panelist preference (0–10 scale) for the horizontally indicated sample over the vertically indicated sample. A negative number indicates the reverse preference. The data for each test of five formulations is shown in TABLES 3, 4, and 5.

TABLE 3

| Formulation Pair Comparison | Base | Example 5 | Example 3 | Example 8 | Example 4 | $\Sigma_r$ |
|---|---|---|---|---|---|---|
| Base (No Clarifier) | X | −5 | 1 | 3 | −5 | 6 |
| Example 5 | 7 | X | −3 | −1 | 0 | −3 |
| Example 3 | −6 | −5 | X | −1 | −2 | 14 |
| Example 8 | 1 | −8 | −3 | X | −9 | 19 |
| Example 4 | 1 | 5 | 1 | 2 | X | −9 |
| $\Sigma_C$ | 3 | −13 | −4 | 3 | −16 | |

TABLE 4

| Formulation Pair Comparison | Example 9 | Example 5 | Example 2 | Example 7 | Dist. Water | $\Sigma_r$ |
|---|---|---|---|---|---|---|
| Example 9 | X | −7 | −5 | −5 | 2 | 15 |
| Example 5 | 4 | X | −3 | −7 | 7 | −1 |
| Example 2 | 4 | 3 | X | 9 | 6 | −22 |
| Example 7 | 7 | −4 | 4 | X | 2 | −9 |
| Distilled Water Control | −2 | −8 | −5 | 6 | X | 9 |
| $\Sigma_C$ | 13 | −16 | 9 | 3 | 17 | |

TABLE 5

| Formulation Pair Comparison | Base | Example 9 | Example 1 | Example 6 | Example 2 | $\Sigma_r$ |
|---|---|---|---|---|---|---|
| Base (No Clarifier) | X | 0 | −3 | −5 | −4 | 12 |
| Example 9 | −2 | X | −1 | −3 | −2 | 8 |
| Example 1 | −4 | 2 | X | −2 | −8 | 12 |
| Example 6 | 6 | 5 | 2 | X | 2 | −15 |
| Example 2 | 7 | 5 | 3 | −2 | X | −13 |
| $\Sigma_C$ | 7 | 12 | 1 | −12 | −12 | |

The data was analyzed by adding the sum of the columns ($\Sigma_c$) to the negative sum of the rows ($\Sigma_r$) to give an overall preference for each formulation ($\Sigma_T$). These are shown from best (least taste) to worst (most taste) in Table 6.

TABLE 6

| Entry | Sample Identification (formulation with:) | Panel Test Preference $(\Sigma_T)$* | Comment |
|---|---|---|---|
| 1 | Distilled Water | 26 | Control - no contact with plastic |
| 2 | Product of Example 9 | 24 | Control - unsubstituted DBS |
| 3 | Product of Example 8 | 22 | Present invention |
| 4 | Base additives only | 14 | Control - no clarifying agent |
| 5 | Product of Example 1 | 13 | Present invention |

TABLE 6-continued

| Entry | Sample Identification (formulation with:) | Panel Test Preference $(\Sigma_T)$* | Comment |
|---|---|---|---|
| 6 | Product of Example 3 | 10 | Comparative example |
| 7 | Product of Example 7 | −6 | Comparative example |
| 8 | Product of Example 5 | −16.5 | Comparative example |
| 9 | Product of Example 2 | −19 | Comparative example |
| 10 | Product of Example 4 | −25 | Comparative example |
| 11 | Product of Example 6 | −27 | Comparative example |

*$\Sigma_T = \Sigma_C + -(\Sigma_r)$

The results from this preliminary screening test show that three of the bis(dialkylbenzylidene)sorbitols (Entries 3, 6, and 7) were rated positively by the taste panel, and that these products were comparable in taste quality to the controls (Entries 1, 2, and 5).

EXAMPLE 12

This Example further demonstrates the improved taste transfer characteristics of the bis(3,4-dialkylbenzylidene)sorbitols over other substitution patterns. Differentiation of the taste transfer characteristics of the best performing bis-dialkylbenzylidene sorbitols from the screening test of Example 11 was obtained through a much narrower taste panel test using only the products of Examples 1 and 8 (3,4-substitution) and Example 3 (2,5-substitution). The basic test protocol and water samples were identical to Example 11. In this case, however, nine taste panelists were used and each panelist compared only two pairs. This was done to improve taste differentiation and prevent taste fatigue. The results from the eighteen blind pair comparisons are shown in matrix form in Table 7 and the overall panel preferences are shown in Table 8.

TABLE 7

| Pair Comparison | Formulation With Example 1 | | Formulation With Example 3 | | Formulation With Example 8 | | $\Sigma_r$ |
|---|---|---|---|---|---|---|---|
| Formulation with Example 1 | X | | 2 −7 −6 | 4 −4 2 | | | 9 |
| Formulation with Example 3 | −1 4 5 | | X | | 1 1 −3 | | −7 |
| Formulation with Example 8 | −4 1 −3 | | −8 −5 −8 | | X | | 27 |
| $\Sigma_C$ | 2 | | −32 | | 1 | | |

TABLE 8

| Entry | Sample Identification (formulation with:) | Panel Test Preference $\Sigma_T$* | Comment |
|---|---|---|---|
| 1 | Product of Example 8 | 28 | Present invention |
| 2 | Product of Example 1 | 11 | Present invention |
| 3 | Product of Example 3 | −39 | Comparative example |

*$\Sigma_T = \Sigma_C - (-\Sigma_r)$

The results clearly show the superiority of the bis(3,4-dialkylbenzylidene)sorbitol acetals in taste transfer characteristics.

What is claimed is:

1. Bis(3,4-dialkylbenzylidene)sorbitol acetals of the formula:

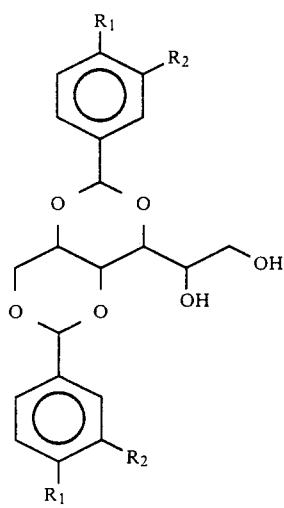

in which $R_1$ and $R_2$ are independently selected from lower alkyl groups containing 1–4 carbon atoms which together form a carbocyclic ring containing up to 5 carbon atoms.

2. The bis(3,4-dialkylbenzylidene sorbitol acetal of claim 1 wherein $R_1$ and $R_2$ together form a carbocyclic ring containing 4 carbon atoms.

3. The bis(3,4-dialkylbenzylidene)sorbitol acetal of claim 2 wherein said sorbitol acetal is 1,3:2,4-Bis(5′,6′,7′,8′-tetrahydro-2-naphthylidene)sorbitol.

4. A polyolefin plastic composition having improved transparency and desirable taste and odor characteristics which comprises a polymer selected from aliphatic polyolefins and copolymers made from at least one aliphatic olefin and one or more ethyleneically unsaturated comonomers, said composition further containing at least one bis(3,4-dialkylbenzylidene)sorbitol acetal of the formula:

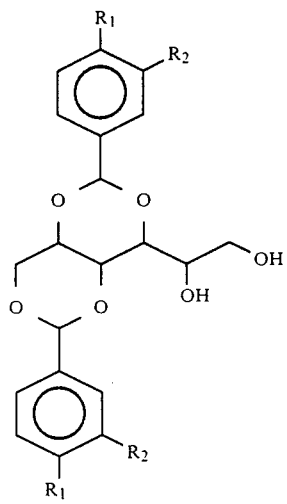

in which $R_1$ and $R_2$ are independently selected from lower alkyl groups containing 1–4 carbon atoms which together form a carbocyclic ring containing up to 5 carbon atoms.

* * * * *